United States Patent
Mitsui

(10) Patent No.: US 10,716,739 B2
(45) Date of Patent: Jul. 21, 2020

(54) STICK-SHAPED COSMETIC

(71) Applicant: TOKIWA CORPORATION, Nakatsugawa-shi, Gifu (JP)

(72) Inventor: Daisuke Mitsui, Kawaguchi (JP)

( * ) Notice: Subject to any disclaimer, the term of this patent is extended or adjusted under 35 U.S.C. 154(b) by 0 days.

(21) Appl. No.: 15/942,577

(22) Filed: Apr. 2, 2018

(65) Prior Publication Data

US 2018/0280255 A1    Oct. 4, 2018

(30) Foreign Application Priority Data

Apr. 4, 2017 (JP) ................................. 2017-074709
Feb. 19, 2018 (JP) ................................. 2018-026687

(51) Int. Cl.

| | | |
|---|---|---|
| *A61K 8/02* | (2006.01) | |
| *A61K 8/86* | (2006.01) | |
| *A61K 8/92* | (2006.01) | |
| *A61Q 1/10* | (2006.01) | |
| *A61Q 1/02* | (2006.01) | |
| *A61K 8/58* | (2006.01) | |
| *A61K 8/31* | (2006.01) | |
| *A61K 8/37* | (2006.01) | |
| *A61K 8/19* | (2006.01) | |
| *A61K 8/25* | (2006.01) | |
| *A61K 8/67* | (2006.01) | |
| *A61K 8/891* | (2006.01) | |
| *A61K 8/81* | (2006.01) | |

(52) U.S. Cl.
CPC .............. *A61K 8/0229* (2013.01); *A61K 8/19* (2013.01); *A61K 8/25* (2013.01); *A61K 8/31* (2013.01); *A61K 8/37* (2013.01); *A61K 8/585* (2013.01); *A61K 8/678* (2013.01); *A61K 8/8152* (2013.01); *A61K 8/86* (2013.01); *A61K 8/891* (2013.01); *A61K 8/922* (2013.01); *A61Q 1/02* (2013.01); *A61Q 1/10* (2013.01); *A61K 2800/43* (2013.01); *A61K 2800/872* (2013.01)

(58) Field of Classification Search
CPC ... A61K 8/31; A61K 8/37; A61K 8/19; A61K 8/25; A61K 2800/872; A61K 8/0229; A61K 8/8152; A61K 8/922; A61K 8/585; A61Q 1/10; A61Q 1/02
See application file for complete search history.

(56) References Cited

U.S. PATENT DOCUMENTS

| | | | | |
|---|---|---|---|---|
| 2003/0035781 A1* | 2/2003 | Minami | .................. | A61K 8/37 424/64 |
| 2004/0013624 A1* | 1/2004 | Mateu | .................. | A61K 8/8111 424/70.7 |
| 2005/0226833 A1* | 10/2005 | Lebre | ..................... | A61K 8/31 424/64 |
| 2009/0142382 A1* | 6/2009 | Shah | ..................... | A61K 8/927 424/401 |
| 2013/0272995 A1* | 10/2013 | Hagiwara | ............... | A61Q 1/06 424/78.35 |

FOREIGN PATENT DOCUMENTS

| | | | |
|---|---|---|---|
| JP | H10-072315 | | 3/1998 |
| JP | 2002-348204 | | 12/2002 |
| JP | 2008-133205 | | 6/2008 |
| JP | 2012-077049 | | 4/2012 |
| JP | 2012077049 | * | 4/2012 |
| JP | 2012077049 A | * | 5/2018 |

OTHER PUBLICATIONS

Unknown author, title: POLYWAX Polyethylenes, product from Baker Hughes, 2011. (Year: 2011).*
Baker Hughes, title: POLYWAX polyethylenes, product information of polywax polyethylenes, 2011. (Year: 2011).*

* cited by examiner

*Primary Examiner* — Yanzhi Zhang
(74) *Attorney, Agent, or Firm* — Soei Patents & Law Firm

(57) ABSTRACT

A stick-shaped cosmetic contains a wax composition including (A) polyethylene wax having an average molecular weight of 600 or more and (B) carnauba wax. Additionally, the stick-shaped cosmetic includes: (C) film-forming agent; (D) volatile silicone oil agent; and (E) powder. The content of the wax composition is 4% to 13% by mass with respect to the total amount of the stick-shaped cosmetic, and the content of (A) polyethylene wax having an average molecular weight of 600 or more in the wax composition is 50% to 95% by mass with respect to the total amount of wax composition.

19 Claims, No Drawings

STICK-SHAPED COSMETIC

CROSS-REFERENCE TO RELATED APPLICATIONS

This application claims the benefits of priority from Japanese Patent Application No. 2017-074709, filed on Apr. 4, 2017, and Japanese Patent Application No. 2018-026687, filed on Feb. 19, 2018, the entire contents of which are incorporated herein by reference.

BACKGROUND OF THE INVENTION

Field of the Invention

The present invention relates to a stick-shaped cosmetic.

Related Background Art

A stick-shaped cosmetic such as eyeliner, eyebrow pencil, lip liner, concealer pencil, or eyeshadow pencil may be provided in a pencil type or a mechanical pencil type cosmetic applicator used by screwing the lead out. The cosmetic is manufactured to have properties of moldability and mechanical strength at the time of production, as well as usability such as uniformity in an applied film, excellent smooth application on the skin, ease of drawing, and suppressed transfer from the skin for exhibiting excellent cosmetic retention effect.

The stick-shaped cosmetic is composed mainly of an oily ingredient containing wax and liquid oil, and a powder such as pigment. The moldability and the usability properties are controlled by adjusting a mixing ratio of the wax and the liquid oil, but it is very difficult to satisfy the moldability and the usability properties for the product at the same time. This is because the smooth application on the skin, cosmetic retention effect, and the like tend to deteriorate if the wax ingredient is blended in large amounts in order to obtain satisfactory moldability, whereas the moldability and mechanical strength tend to deteriorate if an amount of the wax ingredient is reduced in order to obtain satisfactory usability.

In the related art, various contrivances have been made in an effort to have the moldability and the usability properties be compatible in the stick-shaped cosmetic. For example, a method of combining a plurality of waxes, particularly waxes having a high melting point is known in order to obtain sufficient moldability with a small amount of waxes (Japanese Unexamined Patent Publication No. 2002-348204 and Japanese Unexamined Patent Publication No. 2008-133205). A method of using a volatile oil agent or an organic silicone resin is also considered in order to enhance the usability and the cosmetic retention effect (Japanese Unexamined Patent Publication No. 10-72315 and Japanese Unexamined Patent Publication No. 2012-77049).

SUMMARY

In the techniques disclosed in Japanese Unexamined Patent Publication No. 2002-348204 and Japanese Unexamined Patent Publication No. 2008-133205 in which a plurality of waxes are combined, moldability and mechanical strength such as breaking strength and drop resistance cannot be sufficiently satisfied in the stick-shaped cosmetic in which a diameter of the lead is short such as an eyeliner. Furthermore, in the techniques disclosed in Japanese Unexamined Patent Publication No. 10-72315 and Japanese Unexamined Patent Publication No. 2012-77049, the moldability, usability and cosmetic retention properties are improved, but a large amount of wax is blended to make the cosmetic, and thus the feeling of applying the cosmetic is not smooth, and which results in a stiff expression. Especially the skin around the eyes such as the eyelids is softer than other parts of the face, and therefore it is desirable to draw a line with a light force. Even with a soft lead having formulations in which wax having a low hardness is blended in an amount which is sufficient to maintain the shape of the lead, the cosmetic may be broken while being applied, such as when a line is drawn on the skin. Accordingly, smooth application on the skin is poor, an amount of an applied film becomes large, and a quick-drying property deteriorates, which affect the ease of drawing. The prior art cosmetics do not provide sufficient usability such as the ease of drawing and cosmetic retention properties compatible with strength of the cosmetics such as moldability, and therefore further improvement is required.

The present invention has been made in view of the above circumstances, and an object of one or more embodiments of the present invention is to provide a stick-shaped cosmetic in which excellent moldability and mechanical strength are exhibited even if an amount of wax blended is small. Additionally, an object of one or more embodiments of the present invention is to provide a cosmetic having the property that a line can be drawn smoothly with a light force. Further objects of one or more embodiments include providing cosmetics having excellent coloring power, adhesion, and cosmetic retention, in which no transfer from the skin occurs.

The inventors of the present invention have conducted intensive studies and as a result, have found out that among various polyethylene waxes used in the stick-shaped cosmetic, excellent hardness is imparted by a wax composition in which a polyethylene wax having an average molecular weight of 600 or more and a carnauba wax are blended at a specific ratio. In some embodiments, the wax composition is used as a solidifying agent for the stick-shaped cosmetic. In addition, the inventors have found out that by blending the wax composition and specific liquid ingredients or powder ingredients at a specific ratio, excellent moldability and mechanical strength are exhibited even with a small amount of wax blended. Additionally, a line can be drawn smoothly with a light force compared to the cosmetics of the related art, adhesion is favorable after application, transfer resistance is excellent, and coloring power is exhibited even with a thinly applied film. These properties and results may be economically achieved while consuming a smaller amount of the cosmetics as compared to the prior art.

Specifically, one or more embodiments of the present invention include a stick-shaped cosmetic comprising a wax composition comprising (A) polyethylene wax having an average molecular weight of 600 or more and (B) carnauba wax. The stick-shaped cosmetic may additionally comprise (C) film-forming agent; (D) volatile silicone oil agent; and (E) powder. The content of the wax composition may be 4% to 13% by mass with respect to the total amount of the stick-shaped cosmetic. Additionally, the content of (A) polyethylene wax having an average molecular weight of 600 or more in the wax composition may be 50% to 95% by mass.

According to one or more embodiments of the present invention, a stick-shaped cosmetic in which moldability and mechanical strength are exhibited is disclosed, in which a line can be drawn smoothly with a light force compared to the cosmetics of the related art, coloring power is exhibited, adhesion is favorable after application, and a cosmetic retention effect in which no transfer from the skin occurs is excellent.

DESCRIPTION OF THE PREFERRED EMBODIMENTS

Preferred embodiments of the present invention will be described in detail below.

An example stick-shaped cosmetic contains a wax composition that contains (A) polyethylene wax having an average molecular weight of 600 or more (hereinafter referred to as Ingredient (A) in some cases) and (B) carnauba wax (hereinafter referred to as Ingredient (B) in some cases). Additionally, the example stick-shaped cosmetic contains (C) film-forming agent (hereinafter referred to as Ingredient (C) in some cases); (D) volatile silicone oil agent (hereinafter referred to as Ingredient (D) in some cases); and (E) powder (hereinafter referred to as Ingredient (E) in some cases). The content of the wax composition may be 4% to 13% by mass with respect to the total amount of the stick-shaped cosmetic, and the content of Ingredient (A) in the wax composition may be 50% to 95% by mass with respect to the total amount of the wax composition.

In one or more examples of the present invention, the "wax composition" may be understood to refer to a composition composed of Ingredients (A) and (B), and a wax other than Ingredients (A) and (B).

Additionally, the content of the film-forming agent in the stick-shaped cosmetic may be understood as being described in terms of the solid content of the film-forming agent.

In one or more embodiments, the "volatile silicone oil agent" may be understood to disclose a silicone oil agent having a boiling point of 250° C. or lower at 1 atm.

The polyethylene wax of Ingredient (A) used in some example cosmetic products has an average molecular weight of 600 or more from the viewpoint of maintaining moldability and mechanical strength. In cosmetics where an average molecular weight is less than 600, the solidification of the oil ingredient is lowered, and moldability and mechanical strength deteriorate. Even in cosmetics where an amount of wax is blended to maintain sufficient moldability, because the applied cosmetic tends to break at the time of use, the feeling of drawing is not smooth, an applied film becomes thick, and therefore a quick-drying property deteriorates. In cosmetics where an average molecular weight is 750 or more, moldability and mechanical strength tend to be sufficient, but because a melting point becomes extremely high, it is difficult to handle the stick-shaped cosmetic at the time of production. Examples of commercially available products having an average molecular weight of 600 or more include PERFORMALENE 655, PERFORMALENE 725 (manufactured by New Phase Technologies), and the like. Ingredient (A) may be used alone, or two or more kinds thereof may be used in combination.

In some embodiments, the content of Ingredient (A) may be 2% to 12.3% by mass with respect to the total amount of the stick-shaped cosmetic. In other embodiments, the content of Ingredient (A) may be 4% to 11% by mass. In still other embodiments, the content of the Ingredient (A) may be 4.5% to 9% by mass, or 5% to 8% by mass with respect to the total amount of the stick-shaped cosmetic. In some embodiments, one or more properties of the cosmetic may be improved by including a content of Ingredient (A) at one of the increasingly smaller example ranges disclosed above, such as 5% to 8% by mass.

The carnauba wax of Ingredient (B) may comprise a vegetable wax mainly composed of esters of higher fatty acids with higher alcohols and is generally used in cosmetics. In the stick-shaped cosmetic according to the present embodiment, by combining Ingredient (B) with Ingredient (A), a crystal of the wax composition is refined, contributing to improvement in moldability and mechanical strength. The carnauba wax may be obtained by refining a crude natural wax by methods such as degumming treatment, deacidification treatment, hydrogenation method, fractionation method, or column treatment. The refined crude natural wax has less odor and has excellent stability over time. Examples of commercially available refined crude natural wax include purified carnauba wax R-100 (manufactured by YOKOZEKI OIL & FAT INDUSTRIES CO., LTD.), purified carnauba wax NO. 1 (manufactured by CERARICA NODA Co., Ltd.), and the like. The melting point of the carnauba wax is not particularly limited but in some embodiments may be 75° C. or higher.

The content of Ingredient (B) may be 0.2% to 6.5% by mass with respect to the total amount of the stick-shaped cosmetic. In some embodiments, the content of Ingredient (B) may be 0.25% to 5% by mass. In still further embodiments, the content of Ingredient (B) may be 0.3% to 4.5% by mass, or 0.5% to 2.5% by mass with respect to the total amount of the stick-shaped cosmetic. In some embodiments, one or more properties of the cosmetic may be improved by including a content of Ingredient (B) at one of the increasingly smaller example ranges disclosed above, such as 0.5% to 2.5% by mass.

In one or more embodiments, the content of the wax composition, that is, the total content of Ingredients (A) and (B), and the waxes other than Ingredients (A) and (B) may be 4% to 13% by mass, 5% to 11% by mass, 5% to 10% by mass, or 6% to 9% by mass with respect to the total amount of the stick-shaped cosmetic. In some embodiments, one or more properties of the cosmetic may be improved by including a content of the wax composition at one of the increasingly smaller example ranges disclosed above, such as 6% to 9% by mass. In a case where the content is less than 4% by mass, the wax composition does not function satisfactorily as a solidifying agent, which may cause problems in the moldability and mechanical strength of the product in some cases. On the other hand, if the content exceeds 13% by mass, the product may become excessively hard, which results in uneven feeling of drawing and occurrence of stickiness in some cases.

The content of Ingredient (A) in the wax composition may be from 50% to 95% by mass. In some embodiments, the content of Ingredient (A) may be from 60% to 90% by mass. When preparing the wax composition containing Ingredient (A) within these ranges, the hardness of the stick-shaped cosmetic becomes a very high value, and the wax composition exhibits an extremely excellent effect as a solidifying agent. In some embodiments, one or more of these properties may be improved at the smaller range of 60% to 90% by mass as compared to the range of 50% to 95% by mass.

The stick-shaped cosmetic according to one or more embodiments may additionally contain waxes other than Ingredients (A) and (B) as long as the cosmetic properties are not impaired. The waxes other than Ingredients (A) and (B) may include a hydrocarbon wax such as a solid paraffin wax, a ceresin wax, a microcrystalline wax, an ethylene/propylene copolymer, a Fischer Tropsch wax, a polypropylene wax, a montan wax, or an ozokerite wax; a plant-derived wax such as a candelilla wax, a Japan wax, a rice bran wax, or a sunflower wax; an animal-derived wax such as a yellow beeswax or a spermaceti wax; a silicone wax; and the like. The wax other than Ingredients (A) and (B) may be used alone, or two or more kinds thereof may be used in combination. Among these, the plant-derived or the animal-derived wax having a melting point of 65° C. or higher may be used to improve moldability and mechanical strength of products. Examples of such a wax include a candelilla wax, a rice bran wax, a yellow beeswax, and the like, and among these, the candelilla wax is preferable from the viewpoint of moldability in forming the cosmetic within a container ("filling moldability"), for example without creating voids.

In some embodiments, the content of the wax other than Ingredients (A) and (B) may be 0.2% to 1.2% by mass with respect to the total amount of the stick-shaped cosmetic in order to achieve or maintain certain properties of the cosmetic.

The film-forming agent of Ingredient (C) may be selected such that Ingredient (C) contributes to imparting water resistance and oil resistance and improving the cosmetic retention effect. Specific examples thereof include trimethylsiloxysilicate, an acrylic/silicone resin, polyalkylsilsesquioxane, and the like. Ingredient (C) may be used alone, or two or more kinds thereof may be used in combination.

Trimethylsiloxysilicate is a compound having a cross-linked structure with a siloxane structure as a main skeleton and is represented by $[(CH_3\text{-})_3SiO_{1/2}][SiO_2]_y$. Commercially available products include KF-7312F, KF-7312J, KF7312K, KF-7312T, and X-21-5595 (manufactured by Shin-Etsu Chemical Co., Ltd.), in which a volatile oil agent is mixed with a silicone oil.

The acrylic/silicone resin is a polymer in which silicone is modified with a functional group of an acrylic resin. The acrylic/silicone may comprise an (acrylate/polytrimethylsiloxymethacrylate) copolymer, an AMP-(alkyl acrylate/diacetone amide/amodimethicone) copolymer, an (alkyl acrylate/dimethicone) copolymer, an (acrylate/stearyl acrylate/dimethicone methacrylate) copolymer, and the like. Examples of commercially available products include KP-541, KP-543, KP-545, KP-549, KP-550, KP-575, KP-561P, and KP-562P (manufactured by Shin-Etsu Chemical Co., Ltd), and the like.

Polyalkylsilsesquioxane is a branched and crosslinked polymer of an alkyl-modified silicone. The polyalkylsilsesquioxane may comprise polymethylsilsesquioxane, polypropylsilsesquioxane, and the like. Examples of commercially available products include SilForm Flexible resin and SilForm Flexible fluid (manufactured by Momentive Performance Materials Inc.), 670 Fluid (manufactured by Dow Corning Toray Co., Ltd.), and the like.

From the viewpoint of obtaining the stick-shaped cosmetic having excellent moldability and cosmetic retention effect, Ingredient (C) may contain trimethylsiloxysilicate.

The content of Ingredient (C) may be 10% to 40% by mass, 13% to 35% by mass, or 15% to 33% by mass with respect to the total amount of the stick-shaped cosmetic. In some embodiments, one or more properties of the cosmetic may be improved by including a content of Ingredient (C) at one of the increasingly smaller example ranges disclosed above, such as 15% to 33% by mass. In a case where the content is less than 10% by mass, transfer from the skin tends to occur and thus the cosmetic retention effect deteriorates. In a case where the content exceeds 40% by mass, usability such as smooth application on the skin of applied film and ease of drawing may deteriorate.

The volatile silicone oil agent of Ingredient (D) may include a cyclic silicone such as decamethylcyclopentasiloxane or dodecamethylcyclohexasiloxane; a chain silicone such as octamethyltrisiloxane or decamethyltetrasiloxane; a branched silicone such as methyl trimethicone; and the like. Ingredient (D) may be used alone, or two or more kinds thereof may be used in combination.

The content of Ingredient (D) may be 20% to 45% by mass, or 25% to 35% by mass with respect to the total amount of the stick-shaped cosmetic. In some embodiments, one or more properties of the cosmetic may be improved by including a content of Ingredient (D) at the smaller example range of 25% to 35% by mass. In a case where the content is less than 20% by mass, transfer from the skin is likely to occur and thus the cosmetic retention effect deteriorates. In a case where the content exceeds 45% by mass, the stick-shaped cosmetic may have inferior impact resistance.

The powder of Ingredient (E) may be a spherical shape, a plate shape, an acicular shape, an amorphous shape, a fumed shape, a fine particle shape, or the like. The powder may have a particle size of pigment, or may have a porous or nonporous particle structure, and the like.

Specific examples of Ingredient (E) include an inorganic white pigment such as titanium oxide, zinc oxide, cerium oxide, or barium sulfate; an inorganic color pigment such as iron oxide, carbon black, sintered titanium/titanium oxide, chromium oxide, chromium hydroxide, iron blue, or ultramarine blue; a white body powder such as talc, muscovite, phlogopite, lepidolite, biotite, synthetic mica, sericite, synthetic sericite, kaolin, silicon carbide, bentonite, smectite, anhydrous silicic acid, aluminum oxide, magnesium oxide, zirconium oxide, diatomaceous earth, aluminum silicate, magnesium aluminum metasilicate, calcium silicate, barium silicate, magnesium silicate, calcium carbonate, magnesium carbonate, hydroxyapatite, or boron nitride; a glittering powder such as titanium dioxide coated mica, titanium dioxide coated bismuth oxychloride, iron oxide coated mica titanium, iron blue treated mica titanium, carmine treated mica titanium, bismuth oxychloride, fish scale guanine, polyethylene terephthalate/aluminum/epoxy laminated powder, polyethylene terephthalate/polyolefin laminated film powder, or polyethylene terephthalate/polymethyl methacrylate laminated film powder; a synthetic resin powder such as a silicone resin, a polyamide resin, a polyethylene resin, a polyacrylic resin, a polyester resin, a fluorine resin, a cellulose resin, a polystyrene resin, or a styrene-acrylic copolymer resin; an organic polymer resin powder such as polypropylene resin or urethane resin; a low-molecular organic powder such as zinc stearate or N-acyllysine; a natural organic powder such as silk powder or cellulose powder, an organic pigment powder such as Red No. 201, Red No. 202, Red No. 205, Red No. 226, Red No. 228, Orange No. 203, Orange No. 204, Blue No. 404, or Yellow No. 401; an aluminum lake organic pigment powder such as Red No. 3, Red No. 104, Red No. 106, Orange No. 205, Yellow No. 4, Yellow No. 5, Green No. 3, or Blue No. 1; a composite powder such as titanium oxide fine particles coated mica titanium, zinc oxide fine particles coated mica titanium, barium sulfate coated mica titanium, titanium dioxide containing silicon dioxide, or zinc oxide containing silicon dioxide; and the like. Ingredient (E) may be used alone, or two or more kinds thereof may be used in combination. In some embodiments, by using a fluorine compound, a silicone compound, a metal soap, lecithin, hydrogenated lecithin, collagen, hydrocarbon, higher fatty acid, higher alcohol, ester, wax, surfactant, and the like, a powder obtained by surface-treating the powders exemplified above by a known method or a composite powder may be used as Ingredient (E).

The content of Ingredient (E) may be 15% to 42% by mass, or 25% to 40% by mass with respect to the total amount of the stick-shaped cosmetic. In some embodiments, one or more properties of the cosmetic may be improved by including a content of Ingredient (E) at the smaller example range of 25% to 40% by mass. In a case where the content is less than 15% by mass, coloring is insufficient as a cosmetic, and in a case where the content exceeds 42% by mass, the stick-shaped cosmetic becomes a cosmetic having poor smooth application on the skin.

In addition to the above ingredients, ingredients such as oily raw materials, surfactants, preservatives, antioxidants, thickeners, whitening agents, aromatics, moisturizing agents, and skin protective agents, which are generally used in cosmetics, can be blended in the stick-shaped cosmetic within an acceptable range and not impair the properties of the cosmetic. One or two or more of any ingredient can be selected so as to be blended.

The stick-shaped cosmetic according to one or more embodiments may be obtained by blending Ingredients (A), (B), (C), (D), and (E), and other ingredients if necessary, followed by treatment according to a general method. For example, Ingredient (A) and Ingredient (B) are dissolved while being heating, Ingredient (E) is added thereto, the mixture is dispersed by a mill and the like, and then Ingredient (C) and Ingredient (D) are added thereto and uniformly mixed. A molding treatment such as extrusion molding and melt-filling molding is then performed to produce the stick-shaped cosmetic. The stick-shaped cosmetic may contain a volatile silicone oil agent as Ingredient (D), and therefore melt-filling molding using a mold or melt-filling molding in which a cylindrical container is directly filled may be selected.

The hardness of the stick-shaped cosmetic according to the present embodiment may be 0.5 to 2.5 N, or 0.8 to 2.0 N. In some embodiments, one or more properties of the cosmetic may be improved by including a hardness at the smaller example range of 0.8 to 2.0 N, such as from the viewpoint of reduced breakage at the time of use and moldability. In a case where the hardness is within one or the above ranges, the cosmetic is moldable at the time of manufacture, reducing the likelihood of breakage at the time of use or carrying, and the line can be drawn with a light force at the time of application. The term "hardness" refers to a maximum value of a degree of penetration of a measurement sample of the stick-shaped cosmetic. The degree of penetration may be measured under conditions of a pressure-sensitive shaft of 1 mmϕ, a penetration speed of 6 cm/min, and a penetration depth of 10 mm by using FUDOH rheometer RT-2002D*D (manufactured by RHEOTECH). The measurement sample may be prepared by filling an ointment jar (volume: 20 mL) with a cosmetic melted by heating or dissolved in a volatile solvent and allowing the jar to left stand at 25° C. overnight so as to be solidified.

Applications of the stick-shaped cosmetic include eye cosmetics such as eyeliner, eyebrow pencil, concealer pencil, and eyeshadow pencil; lip liner; and the like. For example, the stick-shaped cosmetic may be used as an eye cosmetic, such as an eyeliner, by which it is easy to feel a smooth drawing feeling with a light force.

The stick-shaped cosmetic may have excellent moldability and mechanical strength, in which a line can be drawn smoothly with a light force, coloring power is exhibited, adhesion is favorable after application, and a cosmetic retention effect in which no transfer from the skin occurs is excellent. In some embodiments, a stick-shaped cosmetic may be provided in a cosmetic product having an elongated shape, such as a stick-shaped cosmetic product used by screwing the lead out or a pencil type cosmetic product. The shape of the cosmetic is not particularly limited and may be a cylindrical shape, a rod shape elliptical in the cross section, or a rod shape rectangular in the cross section. However, in some embodiments, a cosmetic having a cylindrical shape or a rod shape elliptical in the cross section may be selected to apply the cosmetic on the soft skin around the eyes. In some embodiments, a diameter of a cross section or a shortest diameter passing through the center of the cross section of the stick-shaped cosmetic may be 1 to 7 mm. In addition, the stick-shaped cosmetic may be molded in a shape in which a length thereof is 20 to 200 mm. Furthermore, the cosmetic may have an elongated shape in which a ratio of a diameter of a cross section or a shortest diameter passing through the center of the cross section of the stick-shaped cosmetic, to a length of the cosmetic, is 1:8 or more.

The effect of "drawing smoothly with a light force" may be confirmed by evaluation on a writing test, a consumed amount of the cosmetic, and usability (smooth application on the skin (good smooth application on the skin at the time of application)) carried out in the following examples. The property of "coloring power" may be confirmed by the evaluation on the writing test, and the property of "favorable adhesion" may be confirmed by the evaluation on the writing test and secondary adhesion resistance carried out in the following examples. Additionally, the "cosmetic retention effect" may be confirmed by the evaluation on transfer resistance and usability, such as stickiness (no stickiness at the time of and immediately after application) carried out in the following examples.

EXAMPLE

Hereinafter, various embodiments will be described in more detail with reference to the following examples, but the present invention is not limited thereto.

Examples 1 to 15 and 21, and Comparative Examples 1 to 11 and 13

A stick-shaped cosmetic (eyeliner) having compositions shown in Tables 1 to 3 was produced by the following method.

With respect to the obtained stick-shaped cosmetic, hardness, breaking strength, and drop resistance were measured, the ease of drawing and a consumed amount of the cosmetic were evaluated by a writing test, filling moldability, transfer resistance, and usability were determined. Usability includes both smooth application on the skin (good smooth application on the skin at the time of application) and stickiness (no stickiness at the time of and immediately after application). The results are shown in Tables 1 to 3.

(Production Method)

Ingredients 1 to 6 were heated and dissolved, Ingredients 16 to 21 were added thereto, the mixture was uniformly dispersed and mixed by a mill, and then the remaining ingredients were added thereto, mixed, and stirred. Next, the mixture was defoamed, a mold was filled therewith and cooled, and then the product was taken out from the mold, and therefore an eyeliner having a diameter of 2 mm and a length of 25 mm was molded.

(Evaluation Method)

[Hardness]

An ointment jar 1 having a volume of 20 mL was filled with a cosmetic melted by heating, and with respect to the sample left to stand at 25° C. overnight, the measurement was performed under, conditions of a pressure-sensitive shaft of 1φ, a penetration speed of 6 cm/min, and a penetration depth of 10 mm by using FUDOH rheometer RT-2002D-D (manufactured by RHEOTECH).

<Evaluation Criteria>
A: 0.80 to 2.00 N
B: 0.50 to 0.79 N, or 2.01 to 2.50 N
C: 0.40 to 0.49 N, or 2.51 to 3.00 N
D: Less than 0.40 N, or 3.01 N or more

[Filling Moldability]

The mixture was melted, and the mold was filled therewith so as perform cooling and solidifying, and then the state of the stick-shaped cosmetic taken out was visually determined in four stages.

<Evaluation Criteria>
A: Excellent
B: Some scratches are observed on the surface of the cosmetic
C: Some bending and chipping are observed
D: Defective (the mold is difficult to be filled with the mixture, and the mixture cannot be taken out from the mold and breaks when being taken out)

[Breaking Strength]

A breaking load of the molded stick-shaped cosmetic was measured at a distance of 20 mm between fulcrums by using a rheometer (manufactured by FUDO kougyou, Inc.). Values of appropriate breaking load vary depending on the diameter of the cross section and the shape of the stick-shaped cosmetic, but in the examples and the comparative examples of the present invention, a determination was carried out in three stages in consideration of the feeling on use, breaking at the time of use, and the like.

<Evaluation Criteria>
B: 0.07 to 0.18 N
C: 0.05 to 0.06 N, or 0.19 to 0.25 N
D: Less than 0.05 N, or 0.26 N or more

[Drop resistance]

The molded stick-shaped cosmetic was inserted to a screw type pencil container and left to stand at 25° C. for 24 hours, and then horizontally dropped five times from a height of 50 cm. This was visually checked, and the determination was performed in four stages.

<Evaluation Criteria>
A: No abnormality
B: Some scratches on the surface of the cosmetic
C: A small amount of chipping (the cosmetic can be screwed out from the container)
D: Breakage and bending (the cosmetic cannot be screwed out from the container)

[Writing Test]

The molded stick-shaped cosmetic was inserted to the screw type pencil container, and a 4 cm line was written twice on BIOSKIN Plate (manufactured by Beaulax) under writing conditions of a writing load of 0.04 N and a writing angle of 90°. The state of the application part after writing was visually observed and determined in four stages.

<Evaluation Criteria>
A: There is no dullness, the drawn line is dark
B: There is no dullness, but the drawn line is light
C: A very small amount of dullness was observed, and the drawn line is light
D: Very dull

[Consumed Amount of Cosmetic]

Writing was performed several times on BIOSKIN Plate until the same degree of darkness was visually observed by the same writing method as in the above Writing Test. A consumed amount of the cosmetic at the end of writing was measured and determined in four stages.

<Evaluation Criteria>
A: 2.0 to 6.0 mg
B: 6.1 to 8.0 mg
C: 8.1 to 10.0 mg
D: More than 10.0 mg

[Transfer Resistance]

The cosmetic was evenly applied on BIOSKIN Plate (manufactured by Beaulax) so as to become 1 cm×3 cm. After 10 minutes, a paper was pressed against the application part, and transfer of the cosmetic was visually observed and determined in four stages.

<Evaluation Criteria>
A: No transfer to the paper
B: A very small amount of transfer on the paper
C: A small amount of transfer on the paper
D: Half or more of the applied cosmetic transfers to the paper

[Usability]

10 specialized panels tested usability on each evaluation item of smooth application on the skin (good smooth application on the skin at the time of application) and stickiness (no stickiness at the time of and immediately after application). An average of points 1 to 5 in five stages of the evaluation (point 1 being the worst, and point 5 being the best) was obtained, and determined based on the following evaluation criteria.

<Evaluation Criteria>
A: The average point is 4.5 or more
B: The average point is 3.5 or more and less than 4.5
C: The average point is 1.5 or more and less than 3.5
D: The average point is less than 1.5

The following commercially available products were used, respectively for the raw materials shown in Tables 1 to 3.

1. Polyethylene wax (molecular weight 655): PERFORMALENE 655 (manufactured by New Phase Technologies, average molecular weight 655)

2. Polyethylene wax (molecular weight 725): PERFORMALENE 725 (manufactured by New Phase Technologies, average molecular weight 725)

3. Polyethylene wax (molecular weight 400): PERFORMALENE 400 (manufactured by New Phase Technologies, average molecular weight 400)

7. Trimethylsiloxysilicate: KF-7312T (manufactured by Shin-Etsu Chemical Co., Ltd.)

8. (Acrylate/stearyl acrylate/dimethicone methacrylate) copolymer: KP-561P (manufactured by Shin-Etsu Chemical Co., Ltd.)

9. Methyl trimethicone: TMF-1.5 (manufactured by Shin-Etsu Chemical Co., Ltd.)

10. Decamethyltetrasiloxane: KF-96L-1.5cs (manufactured by Shin-Etsu Chemical Co., Ltd.)

11. Decamethylcyclopentasiloxane: KF-995 (manufactured by Shin-Etsu Chemical Co., Ltd.)

12. Light isoparaffin: ISODODECANE (manufactured by INEOS Europe Limited)

13. Methyl phenyl polysiloxane: KF-56A (manufactured by Shin-Etsu Chemical Co., Ltd.)

14. Methylpolysiloxane: KF-96A-6cs (manufactured by Shin-Etsu Chemical Co., Ltd.)

15. Diisostearyl malate: COSMOL 222 (manufactured by Nisshin OilliO Group, Ltd.)

TABLE 1

|  |  | Ingredient name | Example 1 | Example 2 | Example 3 | Example 4 | Comparative Example 1 | Comparative Example 2 | Comparative Example 3 | Comparative Example 4 |
|---|---|---|---|---|---|---|---|---|---|---|
| Ingredient (A) | 1 | Polyethylene wax (molecular weight 655) | 5.5 | — | 2.0 | 5.5 | — | 8.0 | 5.5 | 5.5 |
|  | 2 | Polyethylene wax (molecular weight 725) | — | 5.0 | 3.0 | — | — | — | — | — |
|  | 3 | Polyethylene wax (molecular weight 400) | — | — | — | — | 5.5 | — | — | — |
| Ingredient (B) | 4 | Carnauba wax | 2.5 | 2.5 | 2.5 | 1.5 | 2.5 | — | — | — |
|  | 5 | Candelilla wax | — | — | — | 1.0 | — | — | 2.5 | — |
|  | 6 | Yellow beeswax | — | — | — | — | — | — | — | 2.5 |
| Ingredient (C) | 7 | Trimethylsiloxysilicate | 22.0 | 22.0 | 22.0 | 22.0 | 22.0 | 22.0 | 22.0 | 22.0 |
|  | 8 | (Acrylate/stearyl acrylate/dimethicone methacrylate) copolymer | 10.0 | 10.0 | 10.0 | 10.0 | 10.0 | 10.0 | 10.0 | 10.0 |
| Ingredient (D) | 9 | Methyl trimethicone | 27.0 | 27.5 | 27.5 | 27.0 | 27.0 | 27.0 | 27.0 | 27.0 |
|  | 10 | Decamethyltetrasiloxane | — | — | — | — | — | — | — | — |
|  | 11 | Decamethylcyclopentasiloxane | — | — | — | — | — | — | — | — |
|  | 12 | Light isoparaffin | — | — | — | — | — | — | — | — |
|  | 13 | Methyl phenyl polysiloxane | — | — | — | — | — | — | — | — |
|  | 14 | Methylpolysiloxane | — | — | — | — | — | — | — | — |
|  | 15 | Diisostearyl malate | — | — | — | — | — | — | — | — |
| Ingredient (E) | 16 | Black iron oxide | 26.66 | 26.66 | 26.66 | 26.66 | 26.66 | 26.66 | 26.66 | 26.66 |
|  | 17 | Red iron oxide | 0.1 | 0.1 | 0.1 | 0.1 | 0.1 | 0.1 | 0.1 | 0.1 |
|  | 18 | Yellow iron oxide | 0.1 | 0.1 | 0.1 | 0.1 | 0.1 | 0.1 | 0.1 | 0.1 |
|  | 19 | Ultramarine blue pigment | 0.1 | 0.1 | 0.1 | 0.1 | 0.1 | 0.1 | 0.1 | 0.1 |
|  | 20 | Sericite | 5.0 | 5.0 | 5.0 | 5.0 | 5.0 | 5.0 | 5.0 | 5.0 |
|  | 21 | Anhydrous silicic acid | 1.0 | 1.0 | 1.0 | 1.0 | 1.0 | 1.0 | 1.0 | 1.0 |
|  | 22 | Natural vitamin E | 0.04 | 0.04 | 0.04 | 0.04 | 0.04 | 0.04 | 0.04 | 0.04 |
| Evaluation |  | Hardness | A | A | A | A | B | C | B | B |
|  |  | (measurement value (N)) | 0.95 | 1.10 | 1.08 | 0.93 | 0.78 | 0.45 | 0.78 | 0.62 |
|  |  | Filling moldability | A | A | A | A | C | C | C | C |
|  |  | Breaking strength | B | B | B | B | C | C | C | C |
|  |  | (measurement value (N)) | 0.11 | 0.12 | 0.12 | 0.11 | 0.06 | 0.05 | 0.06 | 0.06 |
|  |  | Drop resistance | A | A | A | A | C | D | C | D |
|  |  | Writing test | A | A | A | A | A | A | A | A |
|  |  | Consumed amount of cosmetic | A | A | A | A | C | C | B | D |
|  |  | Transfer resistance | A | A | A | A | A | A | A | A |
|  |  | Usability | A | A | A | A | B | D | C | D |

TABLE 2

|  |  | Ingredient name | Example 5 | Example 6 | Example 7 | Example 8 | Example 9 | Comparative Example 5 | Comparative Example 6 | Comparative Example 7 |
|---|---|---|---|---|---|---|---|---|---|---|
| Ingredient (A) | 1 | Polyethylene wax (molecular weight 655) | 7.0 | 4.0 | 5.5 | 7.6 | 4.0 | 3.0 | 7.8 | 10.0 |
|  | 2 | Polyethylene wax (molecular weight 725) | — | — | — | — | — | — | — | — |
|  | 3 | Polyethylene wax (molecular weight 400) | — | — | — | — | — | — | — | — |
| Ingredient (B) | 4 | Carnauba wax | 5.0 | 1.0 | 2.5 | 0.4 | 4.0 | 5.0 | 0.2 | 5.0 |
|  | 5 | Candelilla wax | — | — | — | — | — | — | — | — |
|  | 6 | Yellow beeswax | — | — | 3.0 | — | — | — | — | — |
| Ingredient (C) | 7 | Trimethylsiloxysilicate | 22.0 | 22.0 | 22.0 | 22.0 | 22.0 | 22.0 | 22.0 | 22.0 |
|  | 8 | (Acrylate/stearyl acrylate/dimethicone methacrylate) copolymer | 10.0 | 10.0 | 10.0 | 10.0 | 10.0 | 10.0 | 10.0 | 10.0 |
| Ingredient (D) | 9 | Methyl trimethicone | 23.0 | 27.0 | 24.0 | 27.0 | 27.0 | 27.0 | 27.0 | 20.0 |
|  | 10 | Decamethyltetrasiloxane | — | — | — | — | — | — | — | — |
|  | 11 | Decamethylcyclopentasiloxane | — | — | — | — | — | — | — | — |
|  | 12 | Light isoparaffin | — | — | — | — | — | — | — | — |
|  | 13 | Methyl phenyl polysiloxane | — | — | — | — | — | — | — | — |
|  | 14 | Methylpolysiloxane | — | — | — | — | — | — | — | — |
|  | 15 | Diisostearyl malate | — | — | — | — | — | — | — | — |
| Ingredient (E) | 16 | Black iron oxide | 26.66 | 26.66 | 26.66 | 26.66 | 26.66 | 26.66 | 26.66 | 26.66 |
|  | 17 | Red iron oxide | 0.1 | 0.1 | 0.1 | 0.1 | 0.1 | 0.1 | 0.1 | 0.1 |
|  | 18 | Yellow iron oxide | 0.1 | 0.1 | 0.1 | 0.1 | 0.1 | 0.1 | 0.1 | 0.1 |
|  | 19 | Ultramarine blue pigment | 0.1 | 0.1 | 0.1 | 0.1 | 0.1 | 0.1 | 0.1 | 0.1 |
|  | 20 | Sericite | 5.0 | 8.0 | 5.0 | 5.0 | 5.0 | 5.0 | 5.0 | 5.0 |

TABLE 2-continued

|  | Ingredient name | Example 5 | Example 6 | Example 7 | Example 8 | Example 9 | Comparative Example 5 | Comparative Example 6 | Comparative Example 7 |
|---|---|---|---|---|---|---|---|---|---|
|  | 21 Anhydrous silicic acid | 1.0 | 1.0 | 1.0 | 1.0 | 1.0 | 1.0 | 1.0 | 1.0 |
|  | 22 Natural vitamin E | 0.04 | 0.04 | 0.04 | 0.04 | 0.04 | 0.04 | 0.04 | 0.04 |
| Evaluation | Hardness | A | B | A | B | B | C | C | D |
|  | (measurement value (N)) | 2.00 | 0.55 | 0.91 | 0.60 | 0.70 | 0.45 | 0.48 | 3.02 |
|  | Filling moldability | A | B | A | B | B | C | C | A |
|  | Breaking strength | B | B | B | B | B | C | C | D |
|  | (measurement value (N)) | 0.18 | 0.07 | 0.10 | 0.07 | 0.08 | 0.05 | 0.05 | 0.34 |
|  | Drop resistance | A | B | B | B | A | D | D | A |
|  | Writing test | B | A | A | A | A | B | A | B |
|  | Consumed amount of cosmetic | B | B | A | A | B | C | C | B |
|  | Transfer resistance | A | A | A | B | A | C | C | B |
|  | Usability | B | B | B | B | B | C | D | D |

Comparative Example 8 was prepared in the same manner as in Comparative Example 1, except that the polyethylene wax of Comparative Example 1 was replaced with the carnauba wax. As a result, the carnauba wax was not uniformly dissolved. Comparative Example 9 in which the polyethylene wax of Example 1 was replaced with Fischer Tropsch wax: SANWAX 171-P (manufactured by Sanyo Chemical Industries, Ltd.) and Comparative Example 10 in which the polyethylene wax of Example 1 was replaced with Microcrystalline Wax: Multiwax (manufactured by Sonneborn LLC.), were prepared in the same manner as in Example 1. As a result, the wax composition was not uniformly dissolved.

TABLE 3

|  |  | Ingredient name | Example 10 | Example 11 | Example 12 | Example 13 | Example 14 | Example 15 | Example 21 | Comparative Example 11 | Comparative Example 13 |
|---|---|---|---|---|---|---|---|---|---|---|---|
| Ingredient (A) | 1 | Polyethylene wax (molecular weight 655) | 7.0 | 5.5 | 7.0 | 5.5 | 5.5 | 5.5 | 8.0 | 5.5 | 5.5 |
|  | 2 | Polyethylene wax (molecular weight 725) | — | — | — | — | — | — | — | — | — |
|  | 3 | Polyethylene wax (molecular weight 400) | — | — | — | — | — | — | — | — | — |
| Ingredient (B) | 4 | Carnauba wax | 3.0 | 2.5 | 1.5 | 2.5 | 2.5 | 2.5 | 3.0 | 2.5 | 2.5 |
|  | 5 | Candelilla wax | — | — | 0.5 | — | — | — | — | — | 0.5 |
|  | 6 | Yellow beeswax | — | — | — | — | — | — | — | — | — |
| Ingredient (C) | 7 | Trimethylsiloxysilicate | 22.0 | 22.0 | 28.0 | 22.0 | 22.0 | 22.0 | 9.0 | 22.0 | 28.0 |
|  | 8 | (Acrylate/stearyl acrylate/dimethicone methacrylate) copolymer | 10.0 | 10.0 | 2.0 | 5.0 | 10.0 | 10.0 | — | 10.0 | 2.0 |
| Ingredient (D) | 9 | Methyl trimethicone | 41.0 | 21.0 | 20.0 | 27.0 | — | — | 30.0 | — | — |
|  | 10 | Decamethyltetrasiloxane | — | — | — | — | 27.0 | — | — | — | — |
|  | 11 | Decamethylcyclopentasiloxane | — | — | — | — | — | 27.0 | — | — | — |
|  | 12 | Light isoparaffin | — | — | — | — | — | — | — | 27.0 | — |
|  | 13 | Methyl phenyl polysiloxane | — | — | 8.0 | — | — | — | — | — | — |
|  | 14 | Methylpolysiloxane | — | — | — | — | — | — | — | — | 28.5 |
|  | 15 | Diisostearyl malate | — | — | — | 5.0 | — | — | 8.0 | — | — |
| Ingredient (E) | 16 | Black iron oxide | 14.66 | 32.66 | 26.66 | 26.66 | 26.66 | 26.66 | 35.66 | 26.66 | 26.66 |
|  | 17 | Red iron oxide | 0.1 | 0.1 | 0.1 | 0.1 | 0.1 | 0.1 | 0.1 | 0.1 | 0.1 |
|  | 18 | Yellow iron oxide | 0.1 | 0.1 | 0.1 | 0.1 | 0.1 | 0.1 | 0.1 | 0.1 | 0.1 |
|  | 19 | Ultramarine blue pigment | 0.1 | 0.1 | 0.1 | 0.1 | 0.1 | 0.1 | 0.1 | 0.1 | 0.1 |
|  | 20 | Sericite | 1.0 | 5.0 | 5.0 | 5.0 | 5.0 | 5.0 | 5.0 | 5.0 | 5.0 |
|  | 21 | Anhydrous silicic acid | 1.0 | 1.0 | 1.0 | 1.0 | 1.0 | 1.0 | 1.0 | 1.0 | 1.0 |
|  | 22 | Natural vitamin E | 0.04 | 0.04 | 0.04 | 0.04 | 0.04 | 0.04 | 0.04 | 0.04 | 0.04 |
| Evaluation |  | Hardness | A | A | A | A | A | A | B | D | B |
|  |  | (measurement value (N)) | 0.80 | 1.50 | 1.68 | 0.81 | 0.93 | 1.11 | 2.08 | 0.10 | 0.60 |
|  |  | Filling moldability | B | A | A | A | A | A | A | D | B |
|  |  | Breaking strength | B | B | B | B | B | B | C | — | B |
|  |  | (measurement value (N)) | 0.10 | 0.17 | 0.16 | 0.09 | 0.10 | 0.12 | 0.23 | — | 0.07 |
|  |  | Drop resistance | B | B | A | A | A | A | A | — | B |
|  |  | Writing test | A | B | A | A | A | B | A | — | A |
|  |  | Consumed amount of cosmetic | B | B | A | A | A | A | A | — | B |
|  |  | Transfer resistance | B | A | A | B | A | A | C | — | D |
|  |  | Usability | B | B | B | B | A | B | A | — | C |

As shown in Tables 1 to 3, the cosmetics obtained in Examples 1 to 15 were evaluated as "A" or "B" in each item of "hardness", "filling moldability", "breaking strength", "drop resistance", "writing test", "consumed amount of the cosmetic", "secondary adhesion resistance", and "usability". The cosmetic obtained in Example 21 was evaluated as "C" in "breaking strength" and "transfer resistance" but evaluated as "A" or "B" in each item of "hardness", "filling moldability", "drop resistance", "writing test", "consumed amount of the cosmetic", and "usability". These are the cosmetics that can be used in practical use without any problem.

On the other hand, as shown in Table 1, in Comparative Example 1 in which an average molecular weight of the polyethylene wax does not satisfy the range specified in the present invention, satisfactory results were not obtained in items of the filling moldability, the breaking strength, the drop resistance, and the consumed amount of the cosmetic. Comparative Examples 2 to 4 in which Ingredient (B) was not blended were not satisfactory not only in the moldability, the mechanical strength, and the consumed amount of the cosmetic but also in the usability. Particularly, in Comparative Example 2 in which only the polyethylene wax was used, a value of bulk hardness was low. Furthermore, as shown in Table 2, in the Comparative Example 5 in which the content of Ingredient (A) in the wax composition is less than 50% by mass, and in the Comparative Example 6, in which the content of Ingredient (A) in the wax composition exceeds 95% by mass, the consumed amount of the cosmetic, the transfer resistance, the usability as well as the moldability and the mechanical strength were not satisfactory. In Comparative Example 7 in which the content of the wax composition exceeds 13% by mass, the bulk hardness, the breaking strength and usability were not satisfactory.

As shown in Table 3, in Comparative Example 11 in which the methyl trimethicone of Ingredient (D) in Example 1 was replaced with the light isoparaffin, the bulk hardness was low, and molding into a rod shape was not possible. In Comparative Example 13 not containing Ingredient (D), a satisfactory result was not obtained in the transfer resistance.

Formulation examples are shown below.

Example 16: Concealer

Ingredients (Blending ratio (% by mass))
1. Polyethylene wax (average molecular weight 655) (7)
2. Carnauba wax (2.5)
3. Sunflower wax (2)
4. Neopentyl glycol diethylhexanoate (5)
5. Cetyl ethylhexanoate (10)
6. Lauryl PEG-9 polydimethylsiloxyethyl dimethicone (3.5)
7. Methyl polysiloxane (2)
8. Natural Vitamin E (0.04)
9. Methyl trimethicone (remainder (33.82))
10. Trimethylsiloxysilicate (12)
11. Methyl hydrogen polysiloxane treated titanium oxide fine particles (8.4)
12. Dimethicone treated zinc oxide fine particles (4.8)
13. Dimethicone treated black iron oxide (0.16)
14. Dimethicone treated red iron oxide (0.36)
15. Dimethicone treated yellow iron oxide (2.42)
16. Dimethicone treated sericite (4)
17. Dimethicone treated anhydrous silicic acid (2)
(Production Method)
Ingredients 1 to 8 were heated and dissolved; Ingredients 11 to 17 were added thereto, the mixture was uniformly dispersed and mixed by a mill, and then the remaining ingredients were added thereto, heated, mixed, and stirred. Next, the mixture was defoamed, a cylindrical container having an inner diameter of 3ϕ was directly filled therewith so as to perform cooling and solidifying, and therefore a stick-shaped concealer having a diameter of 3 mm and a length of 35 mm was molded.

The stick-shaped concealer of Example 16 is a cosmetic which forms a cosmetic film having excellent filling moldability and mechanical strength, smooth application on the skin with a light force and good coloring on the skin, and excellent long-lasting property, by which transfer of the cosmetic becomes less and usability is excellent.

Example 17: Eyebrow Pencil

Ingredients (Blending ratio (% by mass))
1. Polyethylene wax (average molecular weight 655) (8)
2. Carnauba wax (1.8)
3. Rice bran wax (1.2)
4. (Acrylate/stearyl acrylate/dimethicone methacrylate) copolymer (10)
5. Sorbitan Sesquiisostearate (1.0)
6. Natural Vitamin E (0.04)
7. Methyl trimethicone (remainder (29.36))
8. Trimethylsiloxysilicate (17.5)
9. Dimethicone treated black iron oxide (2.6)
10. Dimethicone treatment red iron oxide (1.7)
11. Dimethicone treated yellow iron oxide (1.8)
12. Dimethicone treated sericite (2)
13. Mica Black (8)
14. Polymethylmethacrylate (15)
(Production Method)
Ingredients 1 to 6 were heated and dissolved, Ingredients 9 to 14 were added thereto, the mixture was uniformly dispersed and mixed by a mill, and then the remaining ingredients were added thereto, heated, mixed, and stirred. Next, the mixture was defoamed, a mold was filled therewith and cooled, and then the product was taken out from the mold, and therefore an eyebrow pencil having a diameter of 4 mm and a length of 35 mm was molded.

The eyebrow pencil of Example 17 is a cosmetic which forms a cosmetic film having excellent filling moldability and mechanical strength, smooth application on the skin with a light force and good coloring on the skin, and excellent long-lasting property, by which transfer of the cosmetic becomes less and usability is excellent.

Example 18: Eyeshadow Pencil

Ingredients (Blending ratio (% by mass))
1. Polyethylene wax (average molecular weight 655) (6.5)
2. Carnauba wax (1.6)
3. Candelilla wax (1)
4. (Acrylate/stearyl acrylate/dimethicone methacrylate) copolymer (5)
5. Methyl polysiloxane (2)
6. Polyglyceryl-3 polydimethylsiloxyethyl dimethicone (2)
7. Natural Vitamin E (0.04)
8. Methyl trimethicone (remainder (23))
9. Trimethylsiloxysilicate (19)
10. Dimethicone treated black iron oxide (2.9)
11. Dimethicone treated red iron oxide (2.2)
12. Dimethicone treated yellow iron oxide (1)
13. Dimethicone treated sericite (4)
14. Red No. 201 (0.5)
15. Yellow No. 4 aluminum lake (0.5)
16. Dimethicone treated anhydrous silicic acid (1)
17. Red iron oxide coated mica titanium (29.7)
(Production Method)
Ingredients 1 to 7 were heated and dissolved, Ingredients 10 to 15 were added thereto, the mixture was uniformly dispersed and mixed by a mill, and then the remaining ingredients were added thereto, heated, mixed, and stirred. Next, the mixture was defoamed, a mold was filled therewith and cooled, and then the product was taken out from the mold, and therefore an eyeshadow pencil having a diameter of 6 mm and a length of 41 mm was molded.

The eyeshadow pencil of Example 18 is a cosmetic which forms a cosmetic film having excellent filling moldability and mechanical strength, smooth application on the skin with a light force and good coloring on the skin, and excellent long-lasting property, by which transfer of the cosmetic becomes less and usability is excellent.

Example 19: Eyeliner

Ingredients (Blending ratio (% by mass))
1. Polyethylene wax (molecular weight: 655) (7.5)
2. Carnauba wax (1.8)
3. Candelilla wax (0.2)
4. Methyl phenyl polysiloxane (9.0)
5. Dipentaerythrityl pentaisostearate (1.0)
6. Natural Vitamin E (0.04)
7. Trimethylsiloxysilicate (25.0)
8. Methyl trimethicone (remainder)
9. Dimethicone treated black iron oxide (25.0)
10. Dimethicone treatment ultramarine blue pigment (0.5)
11. Dimethicone treated red iron oxide (0.1)
12. Dimethicone treated yellow iron oxide (0.1)
13. Methyl methacrylate crosspolymer (1.0)
(Production Method)

Ingredients 1 to 6 were heated and dissolved, Ingredients 9 to 13 were added thereto, the mixture was uniformly dispersed and mixed by a mill, and then the remaining ingredients were added thereto, heated, mixed, and stirred. Next, the mixture was defoamed, a mold was filled therewith and cooled, and therefore an eyeliner having a diameter of 1.5 mm and a length of 25 mm was molded.

The eyeliner of Example 19 is a cosmetic which forms a cosmetic film having excellent filling moldability and mechanical strength, smooth application on the skin with a light force and good coloring on the skin, and excellent long-lasting property, by which transfer of the cosmetic becomes less and usability is excellent.

Example 20: Eyeliner

Ingredients (Blending ratio (% by mass))
1. Polyethylene wax (molecular weight 655) (6.0)
2. Carnauba wax (1.5)
3. Candelilla wax (1.0)
4. Natural Vitamin E (0.04)
5. Trimethylsiloxysilicate (22.0)
6. (Acrylate/stearyl acrylate/dimethicone methacrylate) copolymer (8.0)
7. Methyl trimethicone (remainder)
8. Dimethicone treated black iron oxide (9.0)
9. Dimethicone treated titanium oxide (1.0)
10. Dimethicone treated red iron oxide (10.7)
11. Dimethicone treated yellow iron oxide (12.0)
(Production method)

Ingredients 1 to 4 were heated and dissolved, Ingredients 8 to 11 were added thereto, the mixture was uniformly dispersed and mixed by a mill, and then the remaining ingredients were added thereto, heated, mixed, and stirred. Next, the mixture was defoamed, a mold was filled therewith and cooled, and therefore an eyeliner having a diameter of 1.5 mm and a length of 25 mm was molded.

The eyeliner of Example 20 is a cosmetic which forms a cosmetic film having excellent filling moldability and mechanical strength, smooth application on the skin with a light force and good coloring on the skin, and excellent long-lasting property, by which transfer of the cosmetic becomes less and usability is excellent.

What is claimed is:

1. A stick-shaped eye cosmetic comprising:
a wax composition comprising (A) a polyethylene wax and (B) a carnauba wax;
(C) a film-forming agent;
(D) a volatile silicone oil agent; and
(E) a powder,
wherein a content of the wax composition is 4% to 13% by mass with respect to a total amount of the stick-shaped eye cosmetic,
wherein a content of the (A) polyethylene wax in the wax composition is 50% to 95% by mass with respect to a total amount of the wax composition, and
wherein the (A) polyethylene wax comprises one or more wax constituents selected from the group consisting of a polyethylene wax having an average molecular weight of 655 and a polyethylene wax having an average molecular weight of 725.

2. The stick-shaped eye cosmetic according to claim 1, wherein a content of the (C) film-forming agent is 10% to 40% by mass with respect to the total amount of the stick-shaped eye cosmetic.

3. The stick-shaped eye cosmetic according to claim 1, wherein a content of the (D) volatile silicone oil agent is 20% to 45% by mass with respect to the total amount of the stick-shaped eye cosmetic.

4. The stick-shaped eye cosmetic according to claim 1, wherein a content of the (E) powder is 15% to 42% by mass with respect to the total amount of the stick-shaped eye cosmetic.

5. The stick-shaped eye cosmetic according to claim 1, wherein a shortest diameter passing through a center of a cross section of the stick-shaped eye cosmetic is 1 to 7 mm.

6. The stick-shaped eye cosmetic according to claim 1, wherein a diameter passing through a center of a cross section of the stick-shaped eye cosmetic is 1 to 7 mm.

7. The stick-shaped eye cosmetic according to claim 6, wherein a ratio of the diameter to a length of the stick-shaped eye cosmetic is 1:8 or more.

8. A stick-shaped eye cosmetic comprising:
4% to 13% by mass of a wax composition comprising (A) a polyethylene wax and (B) a carnauba wax, with respect to a total amount of the stick-shaped eye cosmetic;
10% to 40% by mass of (C) a film-forming agent with respect to the total amount of the stick-shaped eye cosmetic;
20% to 45% by mass of (D) a volatile silicone oil agent with respect to the total amount of the stick-shaped eye cosmetic; and
15% to 42% by mass of (E) a powder with respect to the total amount of the stick-shaped eye cosmetic,
wherein a content of the (A) a polyethylene wax in the wax composition is 50% to 95% by mass with respect to a total amount of the wax composition, and
wherein the (A) polyethylene wax comprises one or more wax constituents selected from the group consisting of a polyethylene wax having an average molecular weight of 655 and a polyethylene wax having an average molecular weight of 725.

9. The stick-shaped eye cosmetic according to claim 8, wherein a content of the (A) polyethylene wax in the wax composition is 2% to 12.3% by mass with respect to the total amount of the stick-shaped eye cosmetic.

10. The stick-shaped eye cosmetic according to claim 8, wherein a content of the (B) carnauba wax in the wax composition is 0.2% to 6.5% by mass with respect to the total amount of the stick-shaped eye cosmetic.

11. The stick-shaped eye cosmetic according to claim 8, wherein a content of the wax composition is 6% to 9% by mass with respect to the total amount of the stick-shaped eye cosmetic.

12. The stick-shaped eye cosmetic according to claim 8, wherein a content of the (C) film-forming agent is 15% to 33% by mass with respect to the total amount of the stick-shaped eye cosmetic.

13. The stick-shaped eye cosmetic according to claim 8, wherein a content of the (D) volatile silicone oil agent is 25% to 35% by mass with respect to the total amount of the stick-shaped eye cosmetic.

14. The stick-shaped eye cosmetic according to claim 8, wherein a content of the (E) powder is 25% to 40% by mass with respect to the total amount of the stick-shaped eye cosmetic.

15. The stick-shaped eye cosmetic according to claim 8, wherein a content of the (A) polyethylene wax in the wax composition is 5% to 8% by mass with respect to the total amount of the stick-shaped eye cosmetic.

16. The stick-shaped eye cosmetic according to claim 8, wherein a content of the (B) carnauba wax in the wax composition is 0.5% to 2.5% by mass with respect to the total amount of the stick-shaped eye cosmetic.

17. The stick-shaped eye cosmetic according to claim 1, wherein a hardness of the stick-shaped eye cosmetic is 0.5 to 2.5 N.

18. The stick-shaped eye cosmetic according to claim 1, wherein the wax composition further comprises a candelilla wax.

19. The stick-shaped eye cosmetic according to claim 1, wherein the wax composition further comprises a wax other than the (A) polyethylene wax and the (B) carnauba wax, and wherein a content of the wax other than the (A) polyethylene wax and the (B) carnauba wax is 0.2% to 1.2% by mass with respect to the total amount of the stick-shaped eye cosmetic.

* * * * *